(12) United States Patent
Soenksen et al.

(10) Patent No.: US 9,349,036 B2
(45) Date of Patent: May 24, 2016

(54) SYSTEM AND METHOD FOR QUALITY ASSURANCE IN PATHOLOGY

(71) Applicant: Leica Biosystems Imaging, Inc., Vista, CA (US)

(72) Inventors: Dirk G. Soenksen, Carlsbad, CA (US); Kathy Zirker-Smith, Mill Valley, CA (US)

(73) Assignee: LEICA BIOSYSTEMS IMAGING, INC., Vista, CA (US)

( * ) Notice: Subject to any disclaimer, the term of this patent is extended or adjusted under 35 U.S.C. 154(b) by 0 days.

(21) Appl. No.: 14/841,548

(22) Filed: Aug. 31, 2015

(65) Prior Publication Data

US 2015/0379327 A1 Dec. 31, 2015

Related U.S. Application Data

(63) Continuation of application No. 14/330,844, filed on Jul. 14, 2014, now Pat. No. 9,122,905, which is a continuation of application No. 14/065,708, filed on Oct. 29, 2013, now Pat. No. 8,885,900, which is a continuation of application No. 13/453,767, filed on Apr. 23, 2012, now Pat. No. 8,571,286, which is a continuation of application No. 12/114,627, filed on May 2, 2008, now Pat. No. 8,165,363.

(60) Provisional application No. 60/916,252, filed on May 4, 2007.

(51) Int. Cl.
*G06T 7/00* (2006.01)
*G06K 9/00* (2006.01)
*G06K 9/03* (2006.01)
*G06T 5/00* (2006.01)
*G02B 21/36* (2006.01)

(52) U.S. Cl.
CPC .......... *G06K 9/00127* (2013.01); *G02B 21/365* (2013.01); *G06K 9/033* (2013.01); *G06T 5/001* (2013.01); *G06T 7/0012* (2013.01); *G06T 2207/10024* (2013.01); *G06T 2207/10056* (2013.01); *G06T 2207/30024* (2013.01)

(58) Field of Classification Search
CPC G06T 7/0012; G06F 19/321; G01N 15/1475; G02B 21/365
USPC ....................................................... 382/128
See application file for complete search history.

(56) References Cited

U.S. PATENT DOCUMENTS 3,643,015 A 2/1972 Davidovits et al.
4,420,566 A 12/1983 Jessop et al.
(Continued)

FOREIGN PATENT DOCUMENTS

EP 0339582 A2 4/1989
EP 0871052 A1 10/1998
(Continued)

OTHER PUBLICATIONS

Adobe Developers Association, "TIFF" revision 6.0, Jun. 3, 1992; Adobe Systems Incorporated, Mountain View, CA, 121 pages.
(Continued)

*Primary Examiner* — Christ Mahoney
(74) *Attorney, Agent, or Firm* — Procopio, Cory, Hargreaves & Savitch LLP

(57) ABSTRACT

Enhancing color(s) in a digital slide image to increase contrast. In an embodiment, a digital slide image of a tissue sample is acquired. The tissue sample is counterstained, such that the digital slide image comprises an image of a first stain and a second stain. The contrast between the first stain and the second stain is increased to enhance the digital slide image.

20 Claims, 2 Drawing Sheets

(56) References Cited

U.S. PATENT DOCUMENTS

| | | | |
|---|---|---|---|
| 4,673,988 A | 6/1987 | Jansson et al. | |
| 4,700,298 A | 10/1987 | Palcic et al. | |
| 4,742,558 A | 5/1988 | Ishibashi et al. | |
| 4,744,642 A | 5/1988 | Yoshinaga et al. | |
| 4,760,385 A | 7/1988 | Jansson et al. | |
| 4,777,525 A | 10/1988 | Preston | |
| 4,845,552 A | 7/1989 | Jaggi et al. | |
| 4,960,999 A | 10/1990 | McKean et al. | |
| 4,987,480 A | 1/1991 | Lippman et al. | |
| 5,086,477 A | 2/1992 | Yu et al. | |
| 5,172,228 A | 12/1992 | Israelsen | |
| 5,187,754 A | 2/1993 | Currin et al. | |
| 5,231,663 A | 7/1993 | Earl et al. | |
| 5,400,145 A | 3/1995 | Suita et al. | |
| 5,412,214 A | 5/1995 | Suzuki et al. | |
| 5,495,535 A | 2/1996 | Smilansky et al. | |
| 5,578,832 A | 11/1996 | Trulson et al. | |
| 5,625,706 A | 4/1997 | Lee et al. | |
| 5,633,948 A | 5/1997 | Kegelmeyer, Jr. | |
| 5,638,459 A | 6/1997 | Rosenlof et al. | |
| 5,644,356 A | 7/1997 | Swinson et al. | |
| 5,671,288 A | 9/1997 | Wilhelm et al. | |
| 5,672,861 A | 9/1997 | Fairley et al. | |
| 5,710,835 A | 1/1998 | Bradley | |
| 5,714,756 A | 2/1998 | Park et al. | |
| 5,790,710 A | 8/1998 | Price et al. | |
| 5,793,969 A | 8/1998 | Kamentsky et al. | |
| 5,796,861 A | 8/1998 | Vogt et al. | |
| 5,834,758 A | 11/1998 | Trulson et al. | |
| 5,845,013 A | 12/1998 | Bouchard et al. | |
| 5,872,591 A | 2/1999 | Truc et al. | |
| 5,912,699 A | 6/1999 | Hayenga et al. | |
| 5,922,282 A | 7/1999 | Ledley | |
| 5,943,122 A | 8/1999 | Holmes | |
| 5,963,314 A | 10/1999 | Worster et al. | |
| 5,968,731 A | 10/1999 | Layne et al. | |
| 5,991,444 A | 11/1999 | Burt et al. | |
| 5,999,662 A | 12/1999 | Burt et al. | |
| 6,002,789 A | 12/1999 | Olsztyn et al. | |
| 6,005,964 A | 12/1999 | Reid et al. | |
| 6,049,421 A | 4/2000 | Raz et al. | |
| 6,078,681 A | 6/2000 | Silver | |
| 6,091,846 A | 7/2000 | Lin et al. | |
| 6,093,681 A | 7/2000 | Ward et al. | |
| 6,101,265 A | 8/2000 | Bacus et al. | |
| 6,198,839 B1 * | 3/2001 | Kuan | G01N 15/1475 128/922 |
| 6,272,235 B1 | 8/2001 | Bacus et al. | |
| 6,327,377 B1 | 12/2001 | Rutenberg et al. | |
| 6,330,348 B1 | 12/2001 | Kerschmann et al. | |
| 6,438,268 B1 | 8/2002 | Cockshott et al. | |
| 6,519,357 B2 | 2/2003 | Takeuchi | |
| 6,656,683 B1 | 12/2003 | Reuben et al. | |
| 6,711,283 B1 | 3/2004 | Soenksen | |
| 6,714,281 B1 | 3/2004 | Amano et al. | |
| 6,947,869 B2 | 9/2005 | Palmadesso et al. | |
| 7,212,667 B1 | 5/2007 | Shin et al | |
| 7,257,268 B2 | 8/2007 | Eichhorn et al. | |
| 7,502,519 B2 | 3/2009 | Eichhorn et al. | |
| 7,657,070 B2 | 2/2010 | Lefebvre | |
| 7,876,940 B2 | 1/2011 | Chung et al. | |
| 8,165,363 B2 * | 4/2012 | Soenksen | G02B 21/365 382/128 |
| 8,571,286 B2 | 10/2013 | Soenksen et al. | |
| 2001/0017941 A1 | 8/2001 | Chaddha | |
| 2003/0228038 A1 | 12/2003 | Douglass et al. | |
| 2004/0101177 A1 | 5/2004 | Zahlmann et al. | |
| 2004/0122708 A1 | 6/2004 | Avinash et al. | |
| 2004/0170325 A1 | 9/2004 | Eichhorn et al. | |
| 2005/0123181 A1 | 6/2005 | Freund et al. | |
| 2006/0007345 A1 | 1/2006 | Olson et al. | |
| 2006/0178833 A1 * | 8/2006 | Bauer | G01N 15/1475 702/19 |
| 2007/0020697 A1 | 1/2007 | Cualing et al. | |
| 2008/0166036 A1 | 7/2008 | Bloom et al. | |

FOREIGN PATENT DOCUMENTS

| | | |
|---|---|---|
| JP | 62135767 | 6/1987 |
| JP | 2005049646 | 2/2005 |
| JP | 2006181242 A | 7/2006 |
| JP | 2008185337 A | 8/2008 |
| WO | 9114342 A1 | 9/1991 |
| WO | 9839728 A1 | 9/1998 |
| WO | 9844446 A1 | 10/1998 |
| WO | 2004044639 A1 | 5/2004 |
| WO | 2004113876 A1 | 12/2004 |
| WO | 2008137667 A1 | 11/2008 |

OTHER PUBLICATIONS

Hamilton, Eric, JPEG File Interchange Format:, Version 1.02, Sep. 1, 1992; C-Cube Microsystem, Milpitas, CA, 9 pages.

Imagery Resolution Assessments and Reporting Standards IRARS Committee, Civil NIIRS Reference Guide, Mar. 1996, 25 pages.

Korean Intellectual Property Office, International Search Report for PCT/US2008/062407, mailed Aug. 28, 2008, 3 pages.

Korean Intellectual Property Office, Written Opinion for PCT/US2008/062407, mailed Aug. 26, 2008, 5 pages.

Supplementary European Search Report dated Nov. 9, 2011 from European Application No. 08747494, 7 pages.

Office Action (Notice of Reasons for Rejection) for related Japanese Patent Application No. 2010-507550, dated Sep. 25, 2012 and corresponding English translation.

Office Action (Notice of Reasons for Rejection) for related Japanese Patent Application No. 2013-169179, dated Jun. 10, 2014 and corresponding English translation.

European Patent Office, Summons to Attend Oral Proceedings Pursuant to Rule 115(1) EPC with EPO Form 2906, issued in corresponding EP Application No. 08747494.6, Dec. 21, 2015.

* cited by examiner

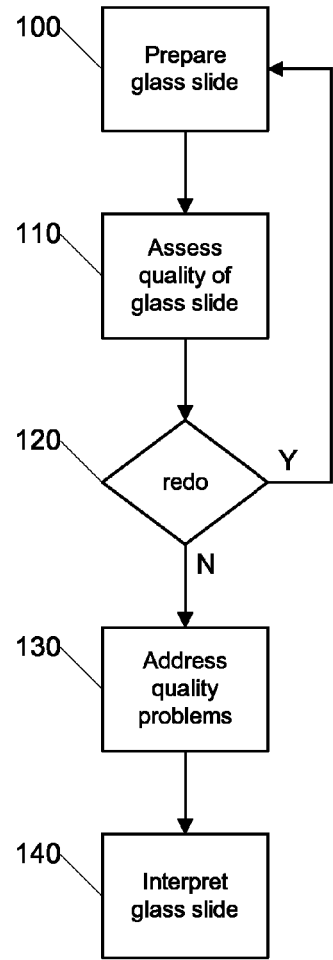
FIG. 1
(PRIOR ART)
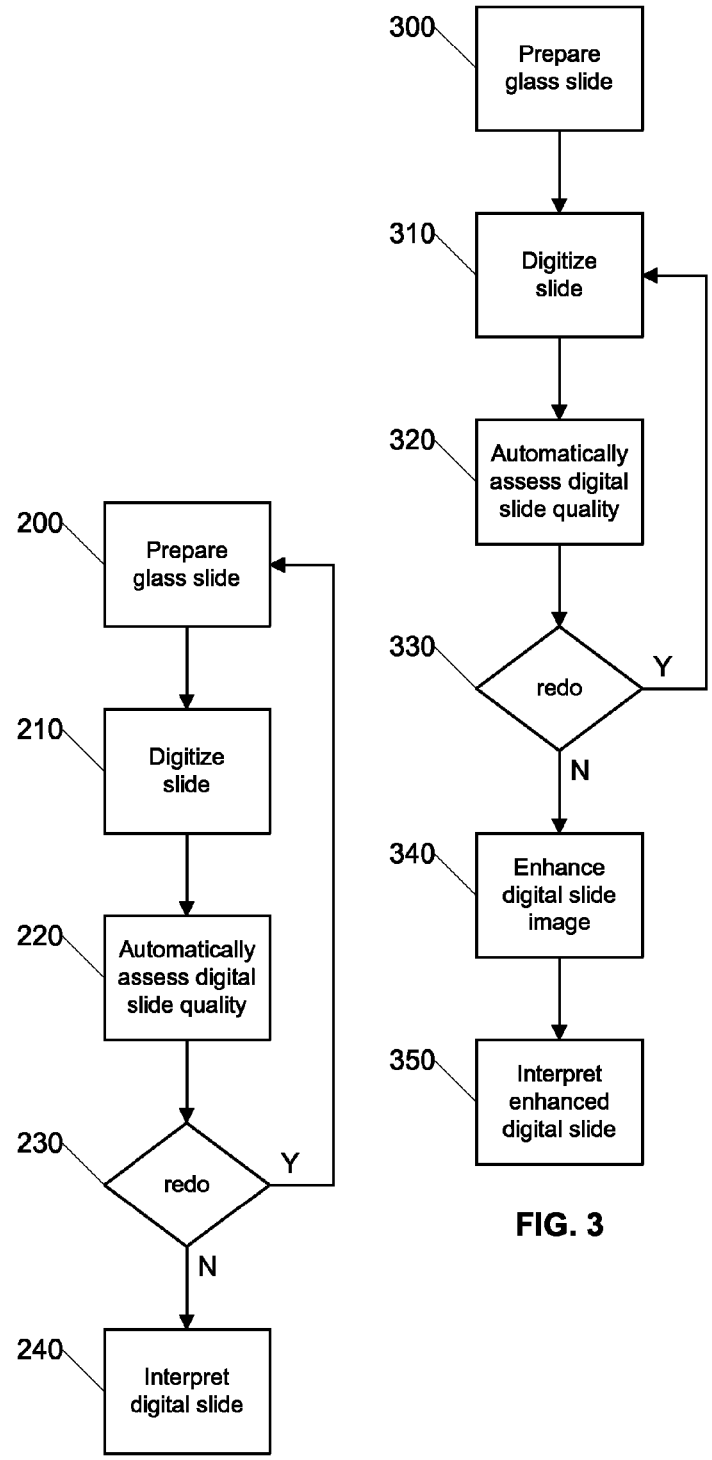
FIG. 2
FIG. 3

SYSTEM AND METHOD FOR QUALITY ASSURANCE IN PATHOLOGY

CROSS-REFERENCE TO RELATED APPLICATIONS

The present application is a continuation of U.S. patent application Ser. No. 14/330,844, filed on Jul. 14, 2014, which is a continuation of U.S. patent application Ser. No. 14/065,708, filed on Oct. 29, 2013 and issued as U.S. Pat. No. 8,885,900, which is a continuation of U.S. patent application Ser. No. 13/453,767, filed on Apr. 23, 2012 and issued as U.S. Pat. No. 8,571,286, which is a continuation of U.S. patent application Ser. No. 12/114,627, filed on May 2, 2008 and issued as U.S. Pat. No. 8,165,363, which claims priority to U.S. Provisional Patent App. No. 60/916,252, filed on May 4, 2007, all of which are hereby incorporated herein by reference in their entireties.

BACKGROUND

1. Field of the Invention

The present invention generally relates to pathology and microscopy and more particularly relates to improvements in quality assurance for pathology using digital microscopy.

2. Related Art

The diagnosis of glass microscope slides by a pathologist is known to be subjective. Many factors contribute to this lack of objectivity, including the training and skill of the pathologist and the quality of the glass slides from which the diagnosis was made. While use of tissue processing instruments and automatic staining equipment has increased the quality and consistency of slide preparations, a significant portion of glass slides that are read by pathologists are still suboptimal and may contribute to inaccurate interpretations.

One of the possible contributing factors to the subjectivity of reading pathology slides is the lack of standardization of the microscope, a tool that has been in use for hundreds of years and which is not recognized as an approved medical device. Pathologists are free to use whatever microscope they want to read glass slides and are expected to know how to keep their microscope in optimal (Koehler) alignment, what objectives lenses with what numerical apertures are best suited for different specimen types, and to be aware when the bulb in their microscope needs to be replaced (because the color temperature of the illuminating light will change the color in the image they observe through the microscope). Many pathologists' microscopes are not maintained in optimal working condition or furnished with optimal objective lenses, thus compromising spatial details and color fidelity that may be essential to making more accurate diagnoses.

Another likely contributing factor to the subjectivity of pathology is deficiencies in glass slide quality, which can include over- or under-staining (i.e., too dark or too light), tissue folds, sections that are too thick or too thin, bubbles, debris as well as variations in image quality observed between slides prepared by different autostainers. There is little a pathologist can do to overcome the challenges of a poorly prepared glass slides ("garbage in/garbage out"), other than to try to make adjustments in the optical properties of the microscope (adjust condenser, increase/decrease light) to try and ameliorate glass slide quality problems.

Referring to FIG. 1, a flow diagram illustrating a conventional process for quality assurance using glass slides is shown. Initially, in step 100 a glass slide is prepared and then in step 110 the quality of the slide is inspected and assessed. In a typical laboratory, a histotechnologist screens the glass slides to assess slide quality, as shown in step 120, and rejects sub-optimal slides before they are read by a pathologist. Rejected slides result in re-cuts and the preparation of new, presumably higher quality, glass slides. In some cases, the slides can be fixed, e.g., by restaining if the staining is too light. This is shown in step 130. Finally, when a glass slide is acceptable, the slide is reviewed and interpreted by a pathologist in step 140.

This conventional process suffers from the inability of the histotechnologist to carefully review every area of a glass slide (some labs process hundreds or thousands of slides every day). The conventional process additionally suffers from the increasing shortage of qualified histotechnologists, and pressure on laboratories to continually improve productivity. Furthermore, the overall aging of the population and the associated increased incidence of cancer (and surgical biopsies) only exacerbate the challenges of quality-assuring glass slides before they are read by a pathologist due to the significant increase in the number of glass slides that are prepared.

Therefore, what is needed is a system and method that overcomes these significant problems found in the conventional systems as described above.

SUMMARY

Accordingly, described herein are systems and methods for improving quality assurance in pathology using digital slide tools for assessing slide quality to trigger (i) preparation of new glass slides, (ii) re-scanning of glass slides, or (iii) enhancement of digital slides prior to interpretation by the pathologist. Digital slides created by slide scanning instruments contribute to improved diagnosis by pathologists by providing an automatic, systematic, objective, and consistent means for digital slide creation and analysis, enabling the use of computer implemented image analysis and image correction tools.

A digital pathology system (slide scanning instrument and software) assesses and improves the quality of a digital slide. The improved digital slide has a higher image quality that results in increased efficiency in the interpretation of such digital slides when they are viewed on a monitor by a pathologist. These improved digital slides yield a more objective diagnosis than reading the corresponding glass slide under a microscope.

Other features and advantages of the present invention will become more readily apparent to those of ordinary skill in the art after reviewing the following detailed description and accompanying drawings.

BRIEF DESCRIPTION OF THE DRAWINGS

The details of the present invention, both as to its structure and operation, may be gleaned in part by study of the accompanying drawings, in which like reference numerals refer to like parts, and in which:

FIG. 1 is a flow diagram illustrating a conventional process for quality assurance using glass slides;

FIG. 2 is a flow diagram illustrating a process for quality assurance using digital slides according to an embodiment of the invention;

FIG. 3 is a flow diagram illustrating an alternative process for quality assurance using digital slides according to an embodiment of the invention;

DETAILED DESCRIPTION

Figure 4:
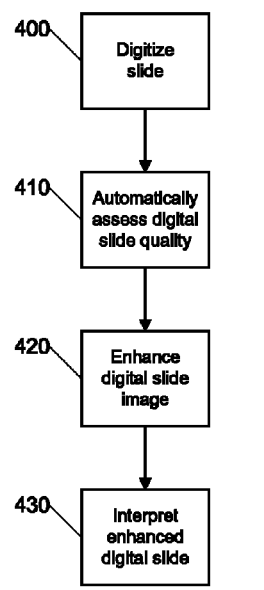
FIG. 4 is a flow diagram illustrating an alternative process for quality assurance using digital slides according to an embodiment of the invention.

Certain embodiments as disclosed herein provide for systems and methods for quality assurance in pathology. After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

FIG. 2 is a flow diagram illustrating a process for quality assurance using digital slides according to an embodiment of the invention. The illustrated process can be carried out by a digital pathology system such as that later described with respect to FIG. 5. Initially, in step 200 the glass slide is prepared in the conventional manner. Next, in step 210 the glass slide is scanned (digitized) to create a high quality digital slide image of the glass slide at a diagnostic resolution for the tissue type. Once the digital slide is created, computer implemented digital slide analysis tools are automatically applied to the slide in step 220 to assess the quality of the digital slide image. For example, the color and focus of a digital slide can be analyzed by quality modules that consider image attributes that include the contrast, brightness and spatial resolution of individual and groups of pixels in the digital slide image. If the quality of the digital slide is insufficient, as determined in step 230, the corresponding glass slide can be rejected and an operator can prepare a new glass slide. If the quality of the digital slide is sufficient for diagnosis, as determined in step 230, then the digital slide can be analyzed and interpreted by a pathologist, who views the digital slide on the monitor at a local or remote viewing station. Alternatively, glass slides in which the quality of the corresponding digital slide is determined to be sufficient by the computer implemented digital slide analysis tools, could be interpreted by a pathologist using a microscope.

In one embodiment, the digital slide quality assessment is made by comparing objective characteristics of the digital slide against a predetermined set of criteria. Advantageously, this provides a consistent and standard level of quality in any digital slide image that can be systematically applied to all digital slides destined for review by a pathologist.

Additionally, in one embodiment the digitizing and automatic assessment of the digital slide may be employed for the sole purpose of removing this task from the histotechnologist, thereby allowing that person to perform other tasks and improve efficiencies. In such an embodiment, the histologist may be notified of borderline quality slides in order to make the final determination of quality for a significantly fewer number of glass slides.

FIG. 3 is a flow diagram illustrating an alternative process for quality assurance using digital slides according to an embodiment of the invention. The illustrated process can be carried out by a digital pathology system such as that later described with respect to FIG. 5. The process in FIG. 3 is initially similar to the process described with respect to FIG. 2 so only the differences will be described here.

Once the glass slide is prepared and digitized and analyzed by the digital slide analysis tools and quality modules, if the quality of the digital slide is insufficient, as determined in step 330, the digital slide image can be rejected and an operator can rescan the glass slide. This can be more efficient if, for example, the digital slide image was rejected due to problems with focus or even problems with too much staining. In one embodiment, a rescan of a glass slide with too much staining can be done with decreased light during scanning in order to account for the over staining. Advantageously, this saves significant time in the overall process and also saves the native tissue source and other goods used in glass slide preparation.

Once a digital image of sufficient quality is created, as determined in step 330, the system next applies computer implemented digital slide enhancement tools to improve the quality of the digital slide image even further, as shown in step 340. For example, the colors of stains can be enhanced or even changed to provide more color contrast in counterstained samples. After the quality assured and image enhanced digital slide is ready, then in step 350 the digital slide can be analyzed and interpreted by a pathologist, who views the digital slide on the monitor at a local or remote reviewing station.

In one embodiment, when a digital slide meets the predetermined quality criteria and is then improved by computer implemented digital enhancement, the improved digital slide is fed into a clinical decision support system that guides the pathologist through the process of making an interpreting the slide in order to arrive at a diagnosis for the slide, or the case associated with the slide.

A few variations in the process shown in FIG. 3 are also possible. For example, if the image quality of the digital slide as determined in step 320 is poor then a new glass slide maybe prepared rather than rescanning the original glass slide. Additionally, providing digital enhancements to the digital slide image is not a necessary step in the process although it provides potentially significantly improved images and can facilitate a more accurate diagnosis by the pathologist.

In one embodiment, the quality assurance system described herein includes using the slide scanning instrument to assess the quality of the glass slide being scanned, and in the event that the glass slide fails predetermined quality criteria, the scanning parameters of the scanning instrument are modified to create a digital slide with improved quality. For example, a slide that is over stained (too dark) would be automatically re-scanned with less light. The determination of whether the glass slide meets predetermined quality criteria can be achieved by initially scanning the glass slide at low or high power and then performing certain types of image analysis on the resulting image to determine, as in the above example, if the slide is too dark.

FIG. 4 is a flow diagram illustrating an alternative process for quality assurance using digital slides according to an embodiment of the invention. The illustrated process can be carried out by a digital pathology system such as that later described with respect to FIG. 5. Initially, in step 400 a glass slide is digitized and then in step 410 the digital slide is automatically evaluated against a set of predetermined criteria to assess the digital slide quality. In step 420, slides that meet or exceed the objective baseline for digital slide quality are then digitally enhanced where possible and then the digital slide is provided to a pathologist for review and analysis, as shown in step 430.

Advantageously, the embodiment shown in FIG. 4 is a highly streamlined computer implemented process. A plurality of slides may be provided to the digital microscopy system for automatic serial or parallel scanning that results in the digital slides being provided to a local or remote pathologist for analysis and diagnosis.

In one embodiment, examples of the types of enhancements made in step 420 to improve the digital slide image prior to diagnosis by a pathologist include enhancement of contrast, color, elimination of defects, and the like including other image processing techniques.

For example, color space standardization can be used to transform the digital slide image into a standardized or non-standardized (and better) color space. Doing so can ensure that digital slides displayed on a monitor appear more consistent in color than the corresponding glass slides would appear under a microscope. Additionally, image processing can apply image enhancement filters (e.g., sharpening, deconvolution, etc.) to the digital slide to enhance spatial details that are not readily apparent to the naked eye. Also, quality assessments can be computed to provide the pathologist an objective computer-generated measure of digital slide quality that informs the pathologist about the underlying integrity of the digital slide. This can be particularly advantageous to a pathologist because knowing that the digital slide quality is suboptimal (e.g., because of poor sample preparation) can be helpful to a pathologist. For example, if the result of a diagnosis of a suboptimal digital slide required surgery, the pathologist may instead order a new glass slide to be prepared and digitized in order to conduct a second review and analysis of the tissue.

Image pattern recognition can also be employed, for example, as part of a decision support system, to automatically identify for a pathologist those regions of a digital slide which have diagnostic significance. This can be very helpful and provide a pathologist with the ability to interrogate regions of one or more digital slides in priority order. Additionally, content based image retrieval can be extremely useful by providing the pathologist with previously diagnosed (i.e., "solved" cases) that have similar image patterns to the digital slide being analyzed. In one embodiment, a database of digital slides or other images can be accessed to retrieve digital slides or other images that show characteristics similar to the digital slide under review.

Figure 5:
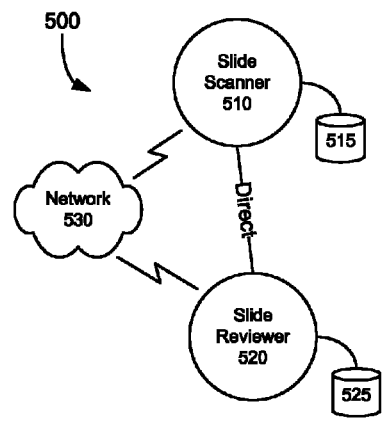
FIG. 5 is a network diagram illustrating a digital pathology system for improved quality assurance in pathology according to an embodiment of the invention.

FIG. 5 is a network diagram illustrating a digital pathology system 500 for improved quality assurance in pathology according to an embodiment of the invention. In the illustrated embodiment, the system 500 comprises a slide scanner 510 that is communicatively coupled with a slide reviewer station 520 via a network 530.

The slide scanner 510 can be any of a variety of digital slide creation systems including image tiling systems, array scanning systems, or line scanning systems, including line scanning systems utilizing time-delay-integration ("TDI"). The line scanning systems are preferred because they create digital slides more rapidly and also because the resulting digital slide images have a much higher quality both in terms of better focus and reduced artifacts such as stitching that are typically introduced by image tiling systems.

The slide scanner functions to digitize a glass slide and store the digital slide in the data storage area 515. Also stored in the data storage area 515 are digital slide analysis tools and modules that can be implemented by the slide scanner 510 to assess the quality of a digital slide. Additionally, digital slide enhancement tools and modules that can be implemented by the slide scanner 510 to improve the quality of a digital slide are also stored in the data storage area 515. These analysis and enhancement tools may also be stored in a separate local or remote data storage area (not shown), for example to conserve processor power at the scanning station and to allow another device to perform the analysis and enhancement functions.

The slide reviewer station 520 can be in communication with the slide scanner 510 either directly (not shown) or via the network 530, which may be a local or wide area network, public or private network, and may or may not include that global combination of networks that is commonly known as the Internet. The slide reviewer station 520 is configured with its own data storage area 525 and allows a pathologist or other analyst (e.g., histotechnologist) to review digital slides that are stored at the slide scanner 510 or at the slide reviewer station 520.

In one embodiment, slides are digitally scanned, their image quality is assessed and slides with sufficient quality are digitally enhanced and then subsequently sent via a network to the reviewing station of a pathologist for analysis. This entire process can be automated, for example by the presence of a barcode on the glass slide that provides information about where the send the enhanced digital slide image for analysis by the pathologist.

Figure 6:
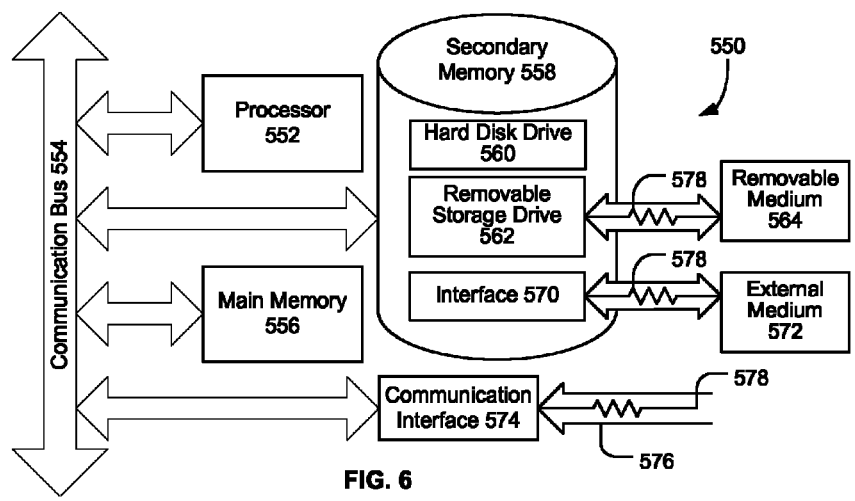
FIG. 6 is a block diagram illustrating an example computer system that may be used in connection with various embodiments described herein.

FIG. 6 is a block diagram illustrating an example computer system 550 that may be used in connection with various embodiments described herein. For example, the computer system 550 may be used in conjunction with the slide scanner system or slide reviewer system previously described with respect to FIG. 5. Other computer systems and/or architectures may also be used, as will be clear to those skilled in the art.

The computer system 550 preferably includes one or more processors, such as processor 552. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 552.

The processor 552 is preferably connected to a communication bus 554. The communication bus 554 may include a data channel for facilitating information transfer between storage and other peripheral components of the computer system 550. The communication bus 554 further may provide a set of signals used for communication with the processor 552, including a data bus, address bus, and control bus (not shown). The communication bus 554 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

Computer system 550 preferably includes a main memory 556 and may also include a secondary memory 558. The main memory 556 provides storage of instructions and data for programs executing on the processor 552. The main memory 556 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 558 may optionally include a hard disk drive 560 and/or a removable storage drive 562, for example a floppy disk drive, a magnetic tape drive, a compact disc ("CD") drive, a digital versatile disc ("DVD") drive, etc. The removable storage drive 562 reads from and/or writes to a removable storage medium 564 in a well-known manner. Removable storage medium 564 may be, for example, a floppy disk, magnetic tape, CD, DVD, etc.

The removable storage medium 564 is preferably a computer readable medium having stored thereon computer executable code (i.e., software) and/or data. The computer software or data stored on the removable storage medium 564 is read into the computer system 550 as electrical communication signals 578.

In alternative embodiments, secondary memory 558 may include other similar means for allowing computer programs or other data or instructions to be loaded into the computer system 550. Such means may include, for example, an external storage medium 572 and an interface 570. Examples of external storage medium 572 may include an external hard disk drive or an external optical drive, or and external magneto-optical drive.

Other examples of secondary memory 558 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage units 572 and interfaces 570, which allow software and data to be transferred from the removable storage unit 572 to the computer system 550.

Computer system 550 may also include a communication interface 574. The communication interface 574 allows software and data to be transferred between computer system 550 and external devices (e.g. printers), networks, or information sources. For example, computer software or executable code may be transferred to computer system 550 from a network server via communication interface 574. Examples of communication interface 574 include a modem, a network interface card ("NIC"), a communications port, a PCMCIA slot and card, an infrared interface, and an IEEE 1394 fire-wire, just to name a few.

Communication interface 574 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via communication interface 574 are generally in the form of electrical communication signals 578. These signals 578 are preferably provided to communication interface 574 via a communication channel 576. Communication channel 576 carries signals 578 and can be implemented using a variety of wired or wireless communication means including wire or cable, fiber optics, conventional phone line, cellular phone link, wireless data communication link, radio frequency (RF) link, or infrared link, just to name a few.

Computer executable code (i.e., computer programs or software) is stored in the main memory 556 and/or the secondary memory 558. Computer programs can also be received via communication interface 574 and stored in the main memory 556 and/or the secondary memory 558. Such computer programs, when executed, enable the computer system 550 to perform the various functions of the present invention as previously described.

In this description, the term "computer readable medium" is used to refer to any media used to provide computer executable code (e.g., software and computer programs) to the computer system 550. Examples of these media include main memory 556, secondary memory 558 (including hard disk drive 560, removable storage medium 564, and external storage medium 572), and any peripheral device communicatively coupled with communication interface 574 (including a network information server or other network device). These computer readable mediums are means for providing executable code, programming instructions, and software to the computer system 550.

In an embodiment that is implemented using software, the software may be stored on a computer readable medium and loaded into computer system 550 by way of removable storage drive 562, interface 570, or communication interface 574. In such an embodiment, the software is loaded into the computer system 550 in the form of electrical communication signals 578. The software, when executed by the processor 552, preferably causes the processor 552 to perform the inventive features and functions previously described herein.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, and methods described in connection with the embodiments disclosed herein can be implemented or performed with a general purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

The invention claimed is:

1. A method comprising using at least one hardware processor to:
   acquire a digital slide image of a tissue sample that is counterstained with at least a first stain and a second stain, such that the digital slide image comprises an image of the first stain and the second stain; and
   increase a contrast between the first stain and the second stain within the digital slide image to enhance the digital slide image.

2. The method of claim 1, wherein increasing the contrast between the first stain and the second stain comprises changing a color of at least one of the first stain and the second stain.

3. The method of claim 1, further comprising using the at least one hardware processor to, prior to increasing the contrast, automatically determine whether or not a quality of the digital slide image is sufficient for diagnosis.

4. The method of claim 3, wherein determining whether or not a quality of the digital slide image is sufficient for diagnosis comprises comparing one or more characteristics of the digital slide image to a predetermined set of one or more criteria.

5. The method of claim 3, wherein increasing the contrast is performed automatically when the determination is that the quality of the digital slide image is sufficient.

6. The method of claim 1, further comprising using the at least one hardware processor to input the enhanced digital slide image into a clinical decision support system that guides a user through an interpretation of the tissue sample to arrive at a diagnosis.

7. A system comprising:
   at least one hardware processor; and
   one or more software modules that, when executed by the at least one hardware processor,
   acquire a digital slide image of a tissue sample that is counterstained with at least a first stain and a second stain, such that the digital slide image comprises an image of the first stain and the second stain, and
   increase a contrast between the first stain and the second stain within the digital slide image to enhance the digital slide image.

8. The system of claim 7, wherein increasing the contrast between the first stain and the second stain comprises changing a color of at least one of the first stain and the second stain.

9. The system of claim 7, wherein the one or more software modules, prior to increasing the contrast, automatically determine whether or not a quality of the digital slide image is sufficient for diagnosis.

10. The system of claim 9, wherein determining whether or not a quality of the digital slide image is sufficient for diagnosis comprises comparing one or more characteristics of the digital slide image to a predetermined set of one or more criteria.

11. The system of claim 9, wherein the one or more software modules increase the contrast automatically when the determination is that the quality of the digital slide image is sufficient.

12. The system of claim 7, wherein the one or more software modules input the enhanced digital slide image into a clinical decision support system that guides a user through an interpretation of the tissue sample to arrive at a diagnosis.

13. The system of claim 7, wherein the at least one hardware processor is comprised in a slide scanner.

14. The system of claim 13, wherein the one or more software modules are stored in a memory of the slide scanner.

15. A non-transitory computer-readable medium having instructions stored thereon, wherein the instructions, when executed by a processor, cause the processor to:
   acquire a digital slide image of a tissue sample that is counterstained with at least a first stain and a second stain, such that the digital slide image comprises an image of the first stain and the second stain; and
   increase a contrast between the first stain and the second stain within the digital slide image to enhance the digital slide image.

16. The non-transitory computer-readable medium of claim 15, wherein increasing the contrast between the first stain and the second stain comprises changing a color of at least one of the first stain and the second stain.

17. The non-transitory computer-readable medium of claim 15, wherein the instructions further cause the processor to, prior to increasing the contrast, automatically determine whether or not a quality of the digital slide image is sufficient for diagnosis.

18. The non-transitory computer-readable medium of claim 17, wherein determining whether or not a quality of the digital slide image is sufficient for diagnosis comprises comparing one or more characteristics of the digital slide image to a predetermined set of one or more criteria.

19. The non-transitory computer-readable medium of claim 17, wherein the instructions cause the processor to increase the contrast automatically when the determination is that the quality of the digital slide image is sufficient.

20. The non-transitory computer-readable medium of claim 15, wherein the instructions further cause the processor to input the enhanced digital slide image into a clinical decision support system that guides a user through an interpretation of the tissue sample to arrive at a diagnosis.

* * * * *